United States Patent [19]

Lundquist

[11] 3,976,402
[45] Aug. 24, 1976

[54] INTRAVENOUS DELIVERY PUMP

[75] Inventor: Ingemar H. Lundquist, Oakland, Calif.

[73] Assignee: Origo, Inc., Hayward, Calif.

[22] Filed: July 15, 1974

[21] Appl. No.: 488,580

[52] U.S. Cl. .................................. 417/566; 417/569; 128/214 E; 222/409; 92/98 D
[51] Int. Cl.² .................................... F04B 21/02
[58] Field of Search ........... 417/566, 559, 569, 571; 128/214 E, 214 F; 92/98 D; 222/409

[56] References Cited
UNITED STATES PATENTS

| | | | |
|---|---|---|---|
| 1,216,460 | 2/1917 | Kilgore | 417/566 |
| 2,402,524 | 6/1946 | Corydon | 417/569 |
| 2,692,618 | 10/1954 | Ludowici | 92/98 D |
| 2,711,134 | 6/1955 | Hughes | 417/566 |
| 2,781,784 | 2/1957 | Baker | 92/98 D |
| 2,791,969 | 5/1957 | Berliner | 417/571 |
| 3,010,404 | 11/1961 | Anderson | 417/566 |
| 3,250,225 | 5/1966 | Taplin | 417/571 |
| 3,354,830 | 11/1967 | Mortara | 417/566 |
| 3,514,218 | 5/1970 | Maher, Jr. | 417/43 |
| 3,701,614 | 10/1972 | Guidicelli | 417/413 |

Primary Examiner—C. J. Husar
Attorney, Agent, or Firm—Flehr, Hohbach, Test, Albritton & Herbert

[57] ABSTRACT

The present invention comprises a small, precise measuring pump provided with a germ barrier that is specifically designed for intravenous feeding devices in which the fluid being pumped is positively displaced; in which there is no rubbing contact of one member with another which would be destructive of blood being pumped; the pumping chambers are small, so that they will hold as little fluid as possible; and in which the valves are actuated by gravity and which are tight-sealing when the pump is in a substantially vertical position, but which, when the pump is tipped on its side, are open to permit the preliminary filling of the pump with the fluid to be pumped.

13 Claims, 3 Drawing Figures

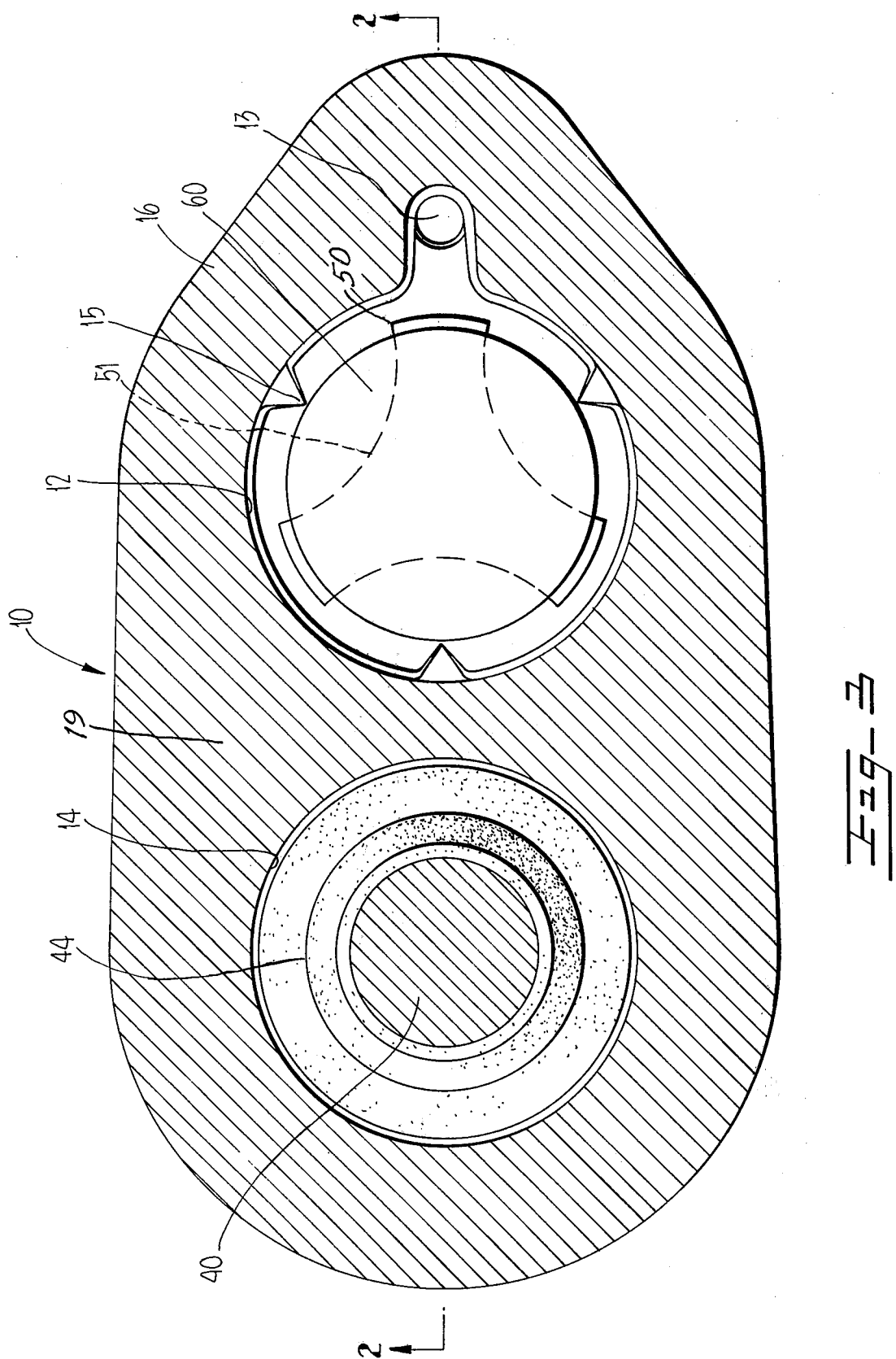

INTRAVENOUS DELIVERY PUMP

BACKGROUND OF THE INVENTION

In recent years there has been considerable interest in intravenous delivery pumps for the feeding of saline solutions, and the like, or blood, to a patient. For many years such materials were fed to a patient only by the force of gravity which necessitated placing the container containing the liquid for delivery to the patient at a considerable elevation above the patient. These devices were not entirely satisfactory in view of the height requirement and the difficulty in accurately regulating their flow. Regulation could only be secured by a hand-set tube clasp, and control was secured by counting the drops of fluid in a predetermined time — and then periodically checking by a nurse to determine that the desired rate of delivery was being maintained. Gravity flow made it very difficult to maintain a regulated flow over a prolonged period of time. Therefore, in recent years there has been a trend toward developing a positive acting pump which could be accurate in its delivery of intravenous feeding material to the patient, could be readily adjusted and would be positive in its operation without requiring the placing of the bottle at some distance above the patient. The pump also should be free from a rubbing contact between parts, as that would be destructive to the pumping of blood. Most pumps heretofore suggested have been rather expensive and hence could not be used once and then thrown away. Such pumps were difficult to disassemble, sterilize and re-assemble so that sterilization and maintenance of sterile conditions are difficult.

In the present invention, the beneficial results are secured by a positive displacement plunger operating in a chamber only slightly larger than the plunger; providing the plunger, which extends through a wall of the chamber, with a resilient sheath sealed to the wall of the chamber so that there could be no contamination from the outside of the material being pumped and there would be no rubbing contact between any member with another where either was in contact with fluid being pumped. The pump is quite small, being approximately only 2 inches in height when viewed from the side, as shown in FIGS. 1 and 2. the pump of the present invention can readily be made of light plastic material, contains few parts, is constructed of material which is relatively inexpensive, so that the pump can be sold cheaply enough to be thrown away with each use.

OBJECTS

It is a primary object of the present invention to provide a small pump particularly adapted for intravenous feeding which is small in size, can readily be made of moldable material, such as Styrene or other plastic, is inexpensive to fabricate and which is extremely accurate in its rate of delivery.

It is another object of the present invention to provide an approved intravenous feeding pump in which there is no rubbing contact between the forcing element and any part of the pump casing, so that it can safely be used for pumping whole blood.

It is a further object of the present invention to provide the pumping element with a germ barrier that prevents the possibility of contamination of the material being pumped and at the same time prevents destruction of blood or other material which is destroyed by the rubbing or shearing contact of one part with another.

It is a further object of the present invention to provide a pump in which the rate of delivery can be readily adjusted by controlling the depth of movement of the plunger into the pumping chamber and by the timing of the separate strokes.

These and other objects of the invention will be apparent from a view of the accompanying drawings when taken in connection with the description which follows.

DRAWINGS

FIG. 3 is an enlarged cross-sectional view of the pump shown in FIG. 1, such as taken along the plane indicated by the line 3—3 of FIG. 1.

Figures 1, 2:
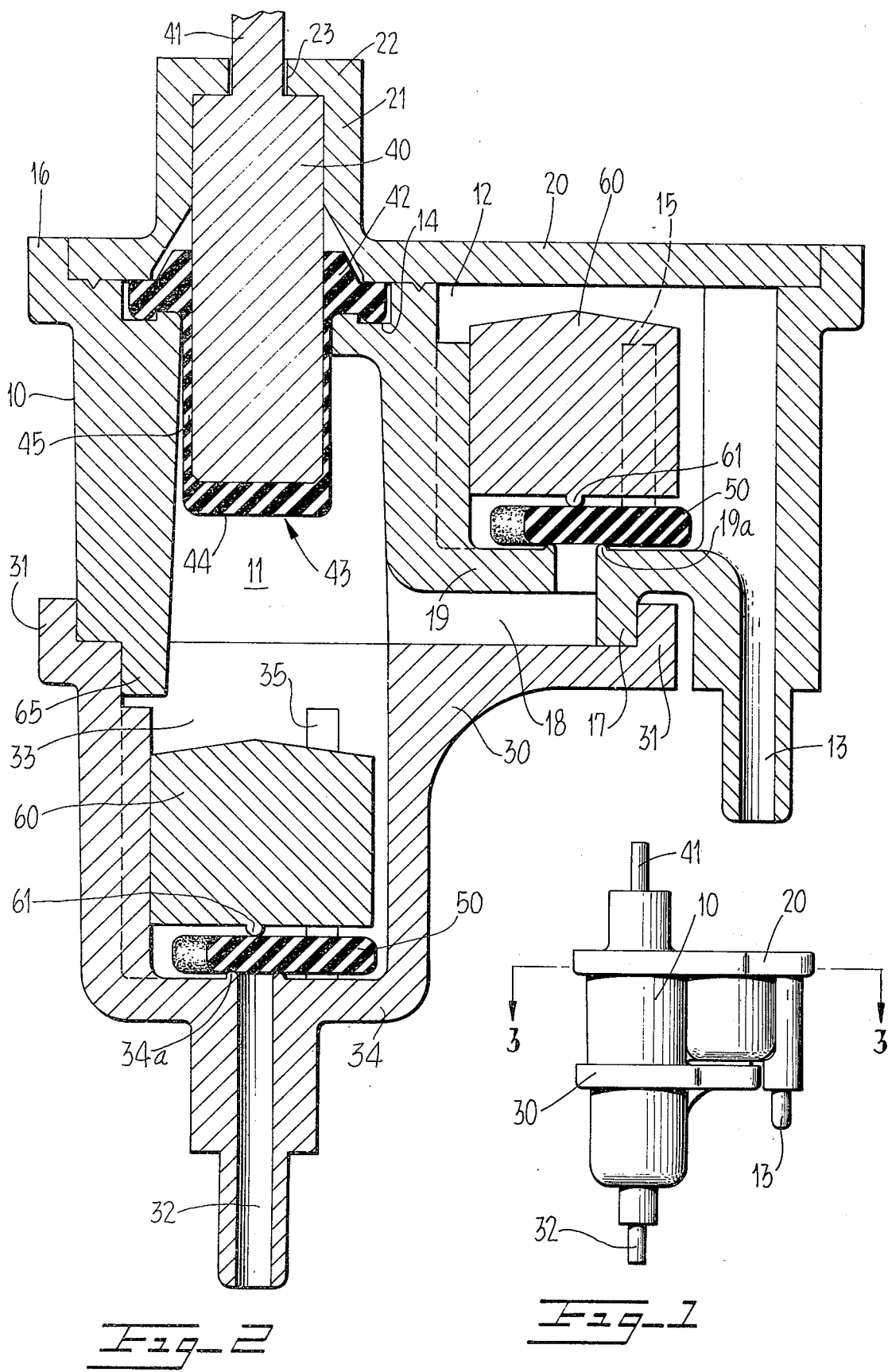
FIG. 1 is a side view of the pump of the present invention.
FIG. 2 is an enlarged cross-sectional side view of the pump of the present invention shown in FIG. 1, such as taken along the plane indicated by the line 2—2 of FIG. 3.

At the outset it should be understood that an intravenous feeding pump must be so designed that it cannot pump air into the patient's blood stream, and which would become inoperative in the event a quantity of air became entrapped therein. It should also be understood that it is preferable that the pump be so constructed that it can either be positively operated or used as a flow-through device merely by changing its position from vertical to horizontal, so that it does not have to be removed from the supply system (with the consequent problems of maintaining sterile conditions) when it is desired to shift from positive operation to gravity feed as may be necessary when moving a patient from one room to another.

In its preferred form the pump of the present invention is formed in three sections: a body 10, a cap 20 and a base plate 30. These sections are each preferably formed of a readily formable hospital grade plastic, such as Styrene, and particularly the kind known as "SAN." Also, it is preferred that they be formed of transparent material so that operation of the interior elements can be seen from the outside.

The body portion of the pump is formed to provide a pumping chamber 11, an outlet chamber 12, and an outlet 13 — the outlet being tubular in form and of a size adapted to readily receive the size of tube usually used to deliver the material to the patient. The pumping chamber 11 and the outlet chamber 12 are separated by a wall 19 having a curtain wall portion which is curved, as shown in FIG. 2, to form circular chambers only slightly larger than the plunger and sheath, and the two valve assemblies to be described later. This wall 19 is provided with a horizontal bottom wall portion which forms the bottom of the outlet chamber, as shown in FIG. 2. There is a sealing well 14 surrounding the pumping chamber 11 adapted to receive the upper end of the plunger sheath 44 to be hereinafter described. The outlet chamber 12 is preferably provided with a plurality, three in the form shown, of aligning ribs 15 adapted to hold the valve weight 60 to be hereinafter described, in proper position. These ribs 15 preferably terminate short of the top of the chamber 12 so as to permit the escape of air while the pump is being filled with fluid prior to operation of the pump. An upper wall 16 adapted to tightly enclose the cover plate 20 surrounds the upper edge of the central body portion 10 and a lower wall 17 is adapted to cooperate with an enclosing wall 31 on the base section 30. A passageway through the separating wall 19 leads from the bottom of the chamber 11 to the bottom of chamber 12.

Preferably, the passageway 18, where it discharges into the bottom of the outlet chamber 12, is provided with an annular bead 19a for cooperation with the valve member 50 to be hereinafter described.

The cap 20 is adapted to fit snugly within the wall 16 of the central section 10. It provides cylindrical wall 21 aligned with the axis of the chamber 11 and is adapted to receive the plunger 40 to be described hereafter. The end of the cylindrical wall, or cap, 21 is closed with a cap 22, as shown in FIG. 2, that is provided with a small opening 23 whereby the plunger 40 can have a stem 41 of reduced diameter extending outwardly through the opening 23 to be actuated by an actuator of the type described in my U.S. Pat. No. 3,798,982, issued Mar. 26, 1974, entitled "Pump Actuator Including Rotatable Cams."

The base portion 30 of the pump body is provided with the upper wall 31 previously mentioned, adapted to fit snugly around the wall 17 of the central section. It is provided with an inlet 32 adapted to have inserted thereover a material delivery tube of the size customarily used in hospitals for the delivery of intravenous feeding materials. The inlet discharges into the bottom of an inlet chamber 33 aligned with the pumping chamber 11 and enclosed by a bottom wall 34 forming a part of the base 30. This chamber also is preferably provided with a plurality of aligning ribs 35 which terminate short of the upper edge of chamber 33. Preferably, also, the inlet 32 is provided with an annular bead 34a which encircles the inlet 32 where it enters the chamber 33.

Positive displacement of the fluid to be pumped is secured by the operation of a plunger 40 which is placed within the pumping chamber 11 and the cylindrical cap 21 of the top member 20. The plunger has a stem 41 extending through the aperture 23 of the cap. The actuating mechanism described in the patent mentioned above is operative to force the stem 41 and plunger 40 inwardly into the chamber 11 a selected distance and at timed intervals, as described in that patent. The plunger 40 is enclosed within a sheath 43, the end 44 of which is thicker than the cylindrical wall section 45. The upper portion 42 of the sheath 43 is provided with a rather large annular flange which is adapted to be squeezed between the cap 20 and the body section 10, whereby it is deformed to provide a completely air-tight and germ-proof shield between the outside atmosphere and the interior of the pump. The sheath 43 is preferably made of a strong and highly elastic rubber-like material, such as a silicon rubber. It is essential that the sheath 43 tightly enclose the plunger 40 at all times so that no air can enter between the sheath and the plunger. It is obvious that if air lies between these two members it will form a bubble which will prevent accurate pumping, as it would, in effect, enlarge the plunger. To return the plunger 40 to its inoperative position, it is preferred that the resilience of the sheath walls 45, which are stretched when the plunger is projected into the chamber 11, will be effective to return it to its inoperative position. Since there will be friction between the plunger and the sheath, it is advisable in most instances to provide a few drops of a suitable lubricant between the plunger and the sheath.

The return force is enhanced if the wall of the plunger 40 or the interior surface of the sheath 43 is dimpled to provide minute pools of lubricant between the two, so that it will not be forced out from between them. It should be mentioned that the upper end of the sheath would fit the plunger so tightly that it is deformed by the insertion of the plunger therein, so that there is no possibility for the entrance of air between the sheath and the plunger. It will be noted that the cylindrical wall 45 of the sheath is thinner than the end wall 44 as mentioned above. This is done to prevent stretching of the sheath from occurring at the end of the plunger as that would tend to form a break in the sheath at the corner of the plunger. Thus, the sheath is stronger at the end where tension would normally be greater, and the tension caused by the stretching of the wall 45 of the sheath will have the advantage not only preventing rupture of the sheath, but also provides a force for the return of the piston to its outward and inactive position.

After the plunger and sheath are placed in the body portion 10, and the placing of the valves 50 and their weights 60 (hereinafter described) in their respective chambers 12 and 33, the cap is placed thereon, the base 30 is placed on the bottom and the three members are attached one to another by cementing, electronic welding, or other suitable process which forms, in effect, an integral structure of the three parts.

The preferred form of valve in the present pump in both the outlet chamber 12 and the inlet chamber 33 comprises a very soft and resilient plate 50. Since it is preferred that both valves be identical, only one will be described particularly. As indicated, the plate 50 is formed of a soft and very resilient rubber composition. Such plates, when pressed down upon the beads 19a or 34a, form a perfect seal. Preferably, these plates are notched, as at 51, to loosely embrace the ribs 15 on the interior of the interior chamber walls 15 or 35. This notching of the valve plate 50 holds the plates from slipping and provides that they always will be properly centered on the end of the duct, except when lifted therefrom by the effect of the pumping operation. Associated with the valve plates 50 is a weight 60 weighing approximately 12 grams, but the weight of which would be accurately computed by a designer to normally close the respective valve, but which would be light enough to be lifted therefrom by operation of the pump. These weights 60 are preferably provided with a small tit 61 which bears against the resilient plate 50. The diameter of the weight 60 is carefully computed to lie within the aligning ribs 15 and 35, so that even if the pump is tilted, the weights will not bind against the walls of their respective chamber when returned to the normal position shown. It is necessary that the weight be always properly aligned in the chamber, regardless of whether the pump is tipped to a horizontal position or not, and that when in a substantially vertical position, it will bear against the valve plate 50 even though the pump is tilted to a considerable angle.

It can be noted at this point that I have found that a weight shaped as shown in the drawings operates most effectively. Thus, a weight with a flat bottom and a central tit provides a better centralized weight on the valve plate 50 than does one with a conical bottom, such as shown on the top of the weights. It can also be mentioned here that it is preferred that the ribs 15 and 35 terminate short of the top of the walls of their respective chambers 12 and 33 to permit the ready escape of air when the pump is being filled before the start of its operation. Finally, it should be noticed that a section 65 of the wall of chamber 11 is enlarged, as shown, to prevent the weight 60 in chamber 33 from getting into chamber 11 when the pump is tilted for it must be kept centralized in chamber 33 at all times.

The operation of the pump will be readily understood. At the outset, the pump is filled with fluid to be pumped, as by turning it from its normal vertical to a substantially horizontal position while connected to the bottle of material to be pumped. When the pump is completely filled as well as the duct leading to the needle to be inserted in the patient's arm, the needle can be inserted, the pump returned to its substantially vertical position and positioned in the pump actuator. While the pump is being filled with liquid, the air with which the pump chamber is filled at the outset will naturally rise to the top (the outlet passage 13). Air can freely escape by the top of the ribs 15 and 35, all of which terminate short of the upper edge of their respective chambers. As long as the outlet 13 is slightly higher than the balance of the pump, the air will all go into the outlet tube, not shown, and will be pushed through the needle before it (the needle) is inserted in the patient. The operation of the pump actuator will depress the stem 41 and hence the plunger 40 into the interior of the pumping chamber 11. Since the liquid is incompressible, it lifts the outlet valve plate 50 and weight 60 to pass material from chamber 11 into chamber 12 and thence into outlet 13. When the pump actuator releases its pressure upon the stem 41 of the plunger, the force of the sheath 45 will return the plunger to the inoperative position shown in FIG. 2. This creates a vacuum in chamber 11, whereupon the suction will lift the valve plate 50 and its weight 60 in the inlet chamber 33 to permit the in-flow of an equal amount of fluid. Thus, the pump will accurately pump a desired quantity of fluid from the source of supply to the patient at measured intervals depending upon the setting of the pump actuator.

It perhaps should be mentioned that in its preferred form the sheath 43 should fit snugly on the plunger 40 so that no air will be trapped between the two. Preferably, the sheath 43 is so proportioned that when the plunger 40 is inserted in the chamber 11, the shoulder 42 between the sheath and the plunger 43 will be compressed between the inside of the outer end of the cap 21 and the sealing well 14 of the body portion 10. At this point the sheath will be relaxed, that is, not under tension but still tightly fitting to the plunger at all points, and since the flange portion 42 of the sheath will be sufficiently deformed to form an air-tight seal with the plunger 40. However, when the pump is placed in its operating position with respect to the pump driver, it is preferred that the piston be moved inwardly slightly so that at that time, but not before, there will be a little tension in the sidewall of the sheath. What must be emphasized is that when a vacuum is created in the chamber 11 by withdrawal of the piston, there must be no air between the plunger and the sheath or the vacuum in the chamber might cause the sheath to bulge and thus might make the pump inaccurate.

It should also be mentioned that in the assembly of the pump it is necessary to place a lubricant on the piston whereby the piston and the sheath can have a sliding contact with each other. It is well-known that rubber has a relatively high coefficient of friction and while some elastic plastics have less, there is still friction between the sheath and the plunger. It is necessary to have as little friction as possible between the two so that the force from the tensioning of the cylindrical wall of the sheath will be sufficient to quickly force the plunger to its most retracted position. I have found that a good grade of silicon lubricant is sufficient for this purpose.

In the event that it is desired to disconnect the pump from its actuator, as when moving a patient from one room to another, and to use it as a "throughflow" device to avoid disconnecting the pump from its inlet and outlet tubes, it can readily be done by turning the pump on its side or upside down. In that position, both valves are disabled as the weights 60 move away from their respective ports and the force from the elevation of the fluid supply is sufficient to cause the throughflow. Thus, so long as the source of material is higher than the patient, the liquid will flow through the inlet 32 and outlet 33 to the patient. Thus, the pump of the present invention, when once filled and connected to a patient, through the conventional delivery tubes, can be used as a pump, or not so used, without disconnecting the pump from either outlet or inlet, or removing the hypodermic needle from the patient.

It will be obvious that many modifications can be made in the arrangement of its parts. For example, the inlet and outlet could be at the left and right ends of the body section 10, respectively, instead of projecting downwardly therefrom.

I claim:
1. A small, precise intravenous pump comprising:
    a. a pump chamber having an inlet into and an outlet from the bottom thereof when the pump is in an operative position;
    b. a plunger having an inner end portion projecting inwardly through a wall of said pump chamber adapted to be moved inwardly and outwardly therein, said plunger having an outer end portion which remains outside of said chamber and is adapted for engagement by a plunger actuating means;
    c. a flexible sheath having the interior surface thereof disposed in close-fitting contact with said inner end portion of said plunger, said sheath having the outer end thereof in sealing engagement with the wall of said pump chamber, and said plunger and sheath being free of rubbing contact with the walls of said chamber;
    d. a valve in said inlet and said outlet which consists of a soft resilient valve plate adapted to engage the interior ends of said ducts; and
    e. weights adapted to force the plates against said inlet and said outlet when said pump is in a vertical position.

2. The apparatus of claim 1 wherein said pump comprises also an outlet chamber laterally adjacent said pumping chamber and the outlet valve is located in the bottom of said chamber.

3. The apparatus of claim 1 wherein the inlet comprises an inlet chamber axially aligned with said pump chamber.

4. The apparatus of claim 1 wherein the inlet comprises an inlet chamber axially with said pump chamber, an outlet chamber laterally adjacent said pump chamber, and a passageway connecting said pump chamber and the bottom of said outlet chamber.

5. The apparatus of claim 4 having an annular bead surrounding the inlet to said inlet chamber and the passageway where it discharges into said outlet chamber.

6. The apparatus of claim 4 having a plurality of aligning ribs in said inlet and outlet chambers.

7. The apparatus of claim 4 wherein said weight is formed with a flat bottom and a small tit adapted to bear against the valve plate at the center of said inlet and said outlet.

8. A small precise intravenous delivery pump comprising:
   a. a pump chamber having an inlet into the bottom thereof when the pump is in an operative position;
   b. an outlet chamber laterally adjacent said pumping chamber having an outlet leading from the bottom thereof;
   c. a passageway from said pump chamber into said outlet chamber leading from an intermediate elevation of said pumping chamber into the bottom of said outlet chamber;
   d. a plunger having an inner end portion projecting inwardly through a wall of said pump chamber adapted to be moved inwardly and outwardly therein, said plunger having an outer end portion which remains outside of said chamber and is adapted for engagement by a plunger actuating means;
   e. a flexible sheath having the interior surface thereof disposed in close-fitting contact with said inner end portion of said plunger, said sheath having the outer end thereof in sealing engagement with the wall of said pump chamber, and said plunger and sheath being free of rubbing contact with the walls of said chamber;
   f. a valve in said pump chamber adapted to close the inlet thereinto and a valve in said outlet chamber adapted to close the passageway into the bottom of said outlet chamber, which valves consist of a soft resilient valve plate adapted to engage the interior ends of said inlet and said passageway; and
   g. weights adapted to force both plates against said inlet and to the end of said passageway when the pump is in a vertical position.

9. A precision liquid delivery pump for delivery of an intravenous liquid to a patient for use with an actuator of a type having a movable member which moved in a controlled manner by the actuator, a housing having an inlet chamber formed therein, said housing being formed with an inlet having an inlet flow passage therein in communication with said inlet chamber and an outlet having an outlet flow passage therein in communication with said inlet chamber, valves means carried by the housing movable between open and closed positions for controlling the flow of liquid through the inlet passage into said inlet chamber, additional valve means carried by the housing movable between open and closed positions for controlling the flow of liquid through the outlet passage from the inlet chamber, means forming a flow passage connected to the outlet and adapted to be connected to the patient, means carried by said housing and adapted to be coupled to said actuator for applying pressure to said liquid in said inlet chamber to cause the same to be forced through the outlet passage against the force of the additional valve means and thereafter removing the pressure from said liquid in said inlet chamber to cause liquid to be drawn through the inlet passage valve means and into the inlet chamber, each of said valve means including a resilient valve member and a weight disposed in the housing for each of said valve members, said pump being positioned so that the force of gravity on the weights serves as sole means for moving the valve members to a closed position independent of the weight of the valve members themselves.

10. A pump as in claim 9 wherein said valve means carried by the housing for causing liquid to pass through said pump includes a piston-like member with a portion of the same being disposed in inlet chamber.

11. A pump as in claim 10 together with means for forming a germ barrier type seal between the piston and the housing.

12. A pump as in claim 9 wherein said weights are formed essentially of metal.

13. The pump as in claim 10 wherein each of said weights is provided with a tit wherein said tit engages the valve member off center with respect to the valve member.

* * * * *